US00PP33439P2

(12) United States Plant Patent
Chaney

(10) Patent No.: US PP33,439 P2
(45) Date of Patent: Aug. 31, 2021

(54) ***TRICYRTIS* PLANT NAMED 'KRISTEN'**

(50) Latin Name: *Tricyrtis formosana*
Varietal Denomination: KRISTEN

(71) Applicant: Christopher Chaney, Fort Mill, SC (US)

(72) Inventor: Christopher Chaney, Fort Mill, SC (US)

( * ) Notice: Subject to any disclaimer, the term of this patent is extended or adjusted under 35 U.S.C. 154(b) by 0 days.

(21) Appl. No.: 17/182,561

(22) Filed: Feb. 23, 2021

(51) Int. Cl.
*A01H 5/02* (2018.01)
*A01H 6/56* (2018.01)

(52) U.S. Cl.
USPC ..... Plt./488
CPC ..... *A01H 6/56* (2018.05)

(58) Field of Classification Search
USPC ..... Plt./488
CPC ..... A01H 5/02
See application file for complete search history.

*Primary Examiner* — Kent L Bell
(74) *Attorney, Agent, or Firm* — Weatherly IP Solutions, LLC; Barbara Campbell

(57) ABSTRACT

A new cultivar of *Tricyrtis* plant named 'KRISTEN' that is distinguishable by spreading plant habit and spring and early summer foliage which is mid-dark green in color and bears bright golden-yellow variegation which is present on approximately 50% of the leaf surface area; by mid-summer, the golden variegation in the foliage of 'KRISTEN' becomes white in color and occupies approximately 20% of the leaf surface area; and the flowers of 'KRISTEN' consist of a star-shaped arrangement of six lavender-pink alternately narrow and wide tepals with yellow bases which together form a yellow throat to each flower, is disclosed.

3 Drawing Sheets

Genus and species: *Tricyrtis formosana.*
Variety denomination: 'KRISTEN'.

BACKGROUND

The present disclosure relates to a new and distinct cultivar of *Tricyrtis* plant, also commonly known as Toad Lily, a perennial plant that is grown for use as an ornamental container plant and for ground cover. The new variety will be referred to hereinafter by the cultivar name 'KRISTEN'.

'KRISTEN' was discovered in March 2019 by the inventor as a naturally-occurring branch sport on one plant of *Tricyrtis formosana* 'Samurai' (not patented). The sport parent plant was growing amongst a crop of 'Samurai' at the inventor's nursery in York, S.C. The inventor observed that the branch sport exhibited variegated leaves with wide and bright golden-yellow edges, whereas the foliage of the growing plants of 'Samurai' is light green in color with narrower and paler yellow margins.

During summer 2019, the inventor excised the new sport branch from its parent plant and made stem cuttings and established new plants on their own roots. Subsequent cuttings were taken and rooted from these first propagations. In all cases, the inventor has determined that the sport cuttings have remained stable in successive generations of asexual propagation. In addition, the inventor has planted cuttings of the new variety in-ground and has observed that new growth from the below-ground rhizomes exhibits identical foliage. The new variety, 'KRISTEN' is stable whether grown from stem cuttings or by division of underground rhizomes.

SUMMARY

The following traits have been repeatedly observed and represent the distinguishing characteristics of 'KRISTEN'.

'KRISTEN' has not been tested under all possible conditions and phenotypic differences may be observed with variations in environmental, climatic, and cultural conditions, without however, any variance in genotype.

1. An established plant of 'KRISTEN' exhibits a spreading plant habit.
2. The newly-emerging spring foliage of 'KRISTEN' grows upright initially and arches at approximately 45 cm to 50 cm in height.
3. The width or spread of a 15 months old plant of 'KRISTEN' varies between 45 cm (container grown) and 60 cm (when established in-ground).
4. By mid-summer plants of 'KRISTEN' exhibit prolific new shoot growth arising from underground rhizomes to create a ground-cover effect.
5. The new spring foliage growth of 'KRISTEN' is mid-dark green in color and bears bright golden-yellow variegation which is present on approximately 50% of the leaf surface area.
6. By mid-summer, the golden variegation in the foliage of 'KRISTEN' becomes white in color and occupies approximately 20% of the leaf surface area.
7. The flowers of 'KRISTEN' are typical of the species and consist of a star-shaped arrangement of six alternately narrow and wide tepals.
8. The tepals of 'KRISTEN' are lavender-pink in color except for the tepal basal area which is yellow and together form a yellow throat to each flower.
9. 'KRISTEN' is hardy at least to USDA Zone 5 and is well-suited to growing in full or partial shade.

DESCRIPTION OF THE PHOTOGRAPHS

The accompanying photographs were taken from plants growing under light shade at a nursery in York, S.C.

DESCRIPTION OF THE NEW VARIETY

Figure 1:
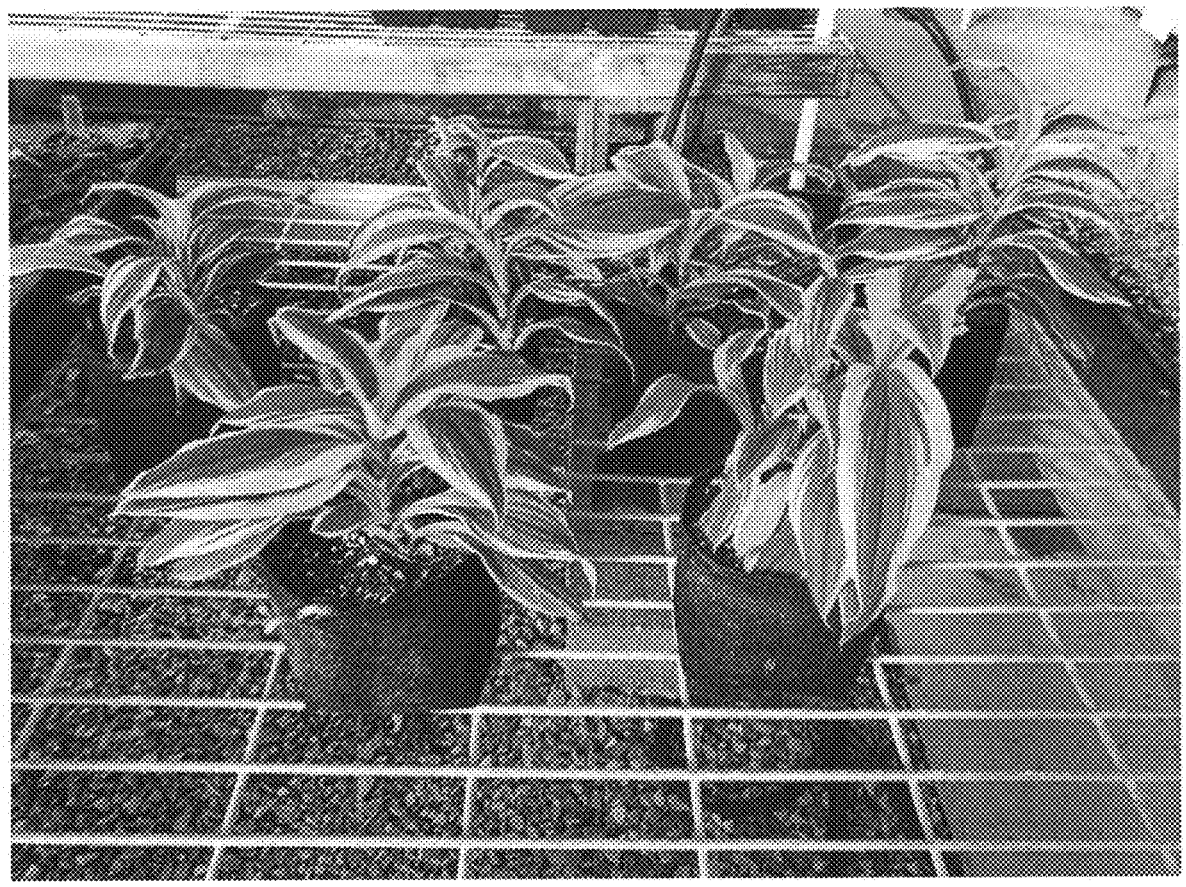
FIG. 1 illustrates the newly-emerging spring growth of 'KRISTEN'.
Figure 2:
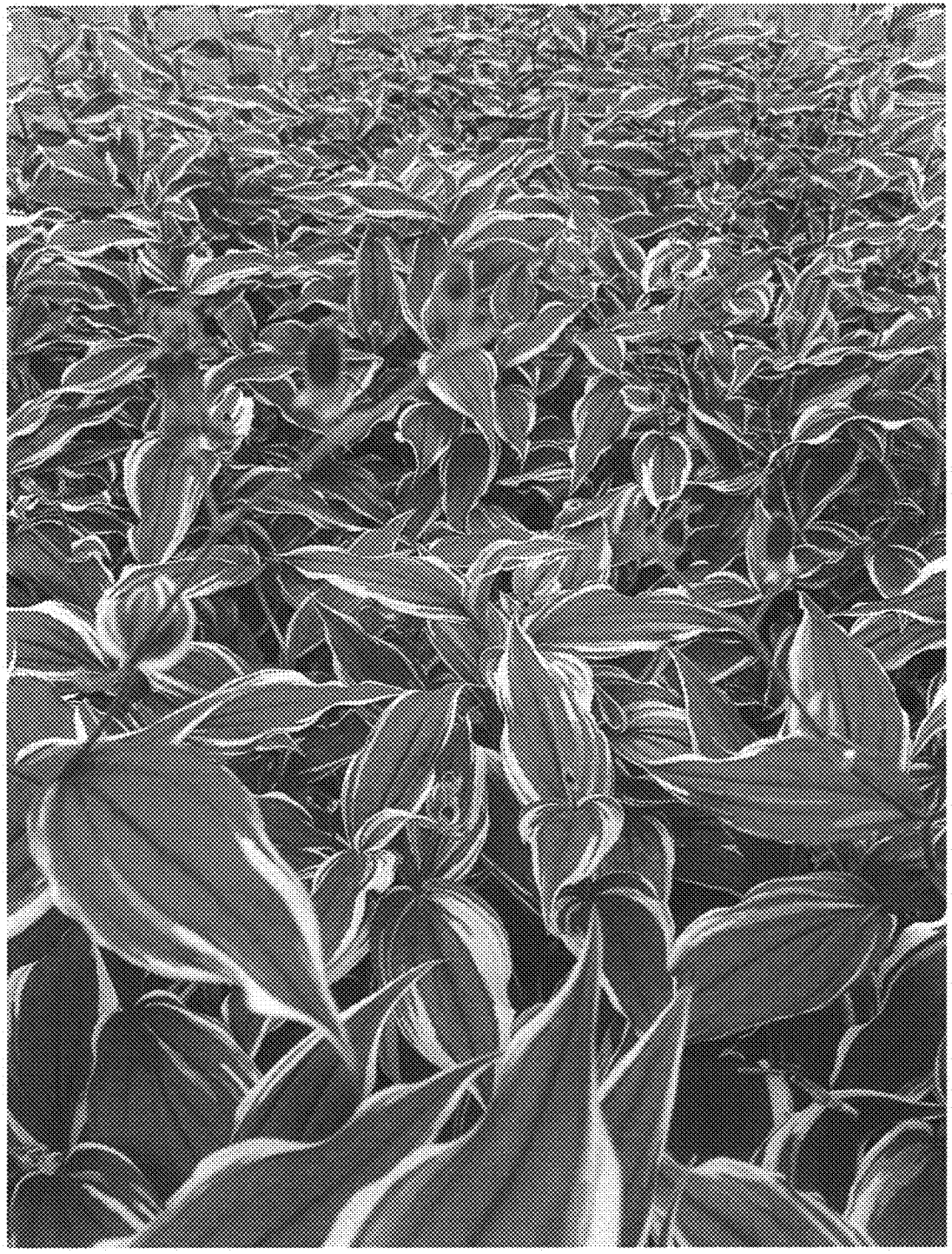
FIG. 2 illustrates the mature foliage of 'KRISTEN' in mid-summer. The foliage has become blue-green and grey-green with reduced area of white variegation.
Figure 3:
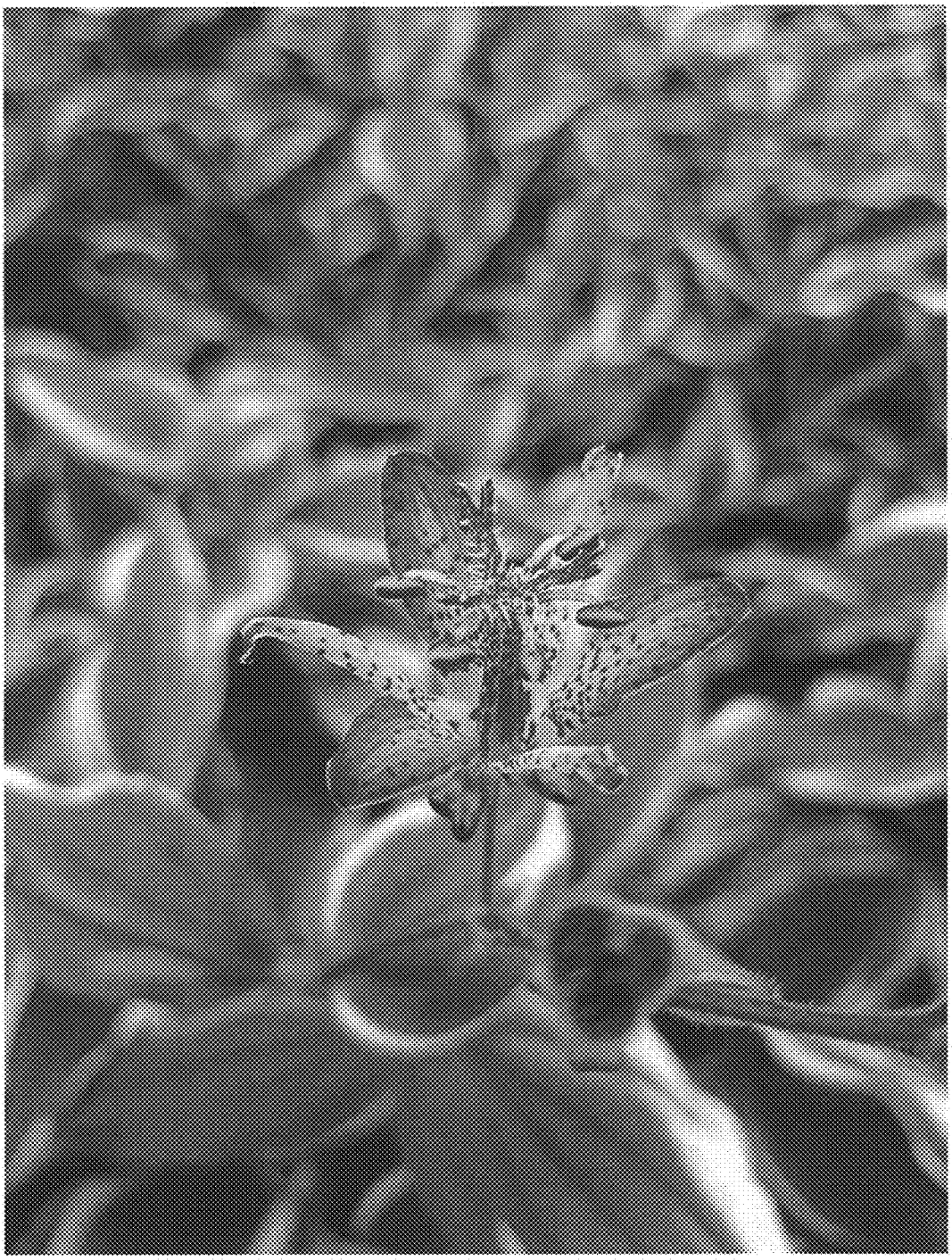
FIG. 3 illustrates a close-up view of the inflorescence of 'KRISTEN' when first in bloom in mid-summer under light shade. The tepals in the inflorescence may take on a more lavender-blue color when exposed to more sunlight.

The following detailed descriptions set forth the distinctive characteristics of 'KRISTEN'. Observations, measurements, values, and comparisons were collected in late spring and summer from 9 to 12 month-old plants which were growing outdoors in partial shade in 1-gallon containers. Color determinations were made in accordance with The 2007 Royal Horticultural Society Colour Chart from London England, except where general color terms of ordinary dictionary significance are used.

Classification:

*Family*.—Convallariaceae (formerly Liliaceae).

*Genus*.—*Tricyrtis*.

*Species*.—*Formosana*.

*Common name*.—Toad Lily.

Parentage: Naturally occurring branch sport of *Tricyrtis formosana* 'Samurai' (unpatented).

Plant:

*Propagation method*.—Stem cuttings, division of rhizomes.

*Rooting system*.—Rhizomatous with fine grey-white adventitious roots.

*Vigor*.—Vigorous stoloniferous growth.

*Time to develop roots*.—Approximately 3 weeks are required for a newly planted division to become established on its own roots.

*Crop time*.—Approximately 14 to 16 weeks are required to fill out a 1-gallon container using rooted cuttings planted in spring. Approximately 9 months if starting with a rooted cutting planted in the fall.

*Suggested container size*.—1 gallon container and larger if desired.

*Use*.—Ornamental for use as a container plant or for planting in the landscape as a ground cover.

*Type*.—Perennial.

*Overall dimensions*.—The newly-emerging spring foliage of 'KRISTEN' grows upright initially and arches at approximately 45 cm to 50 cm in height. The width or spread of a 15-month-old plant of 'KRISTEN' varies between 45 cm (container grown) and 60 cm (when established in-ground).

*Cultural requirements*.—Grow in partial or full shade in moist soils or planting medium.

*Hardiness*.—USDA Zone 5.

*Growth habit*.—Compact, new stems upright then arching and spreading over time.

*Blooming season*.—Mid-summer to fall.

*Lastingness of blooms*.—Once open, individual flowers on the plant remain fresh for 3 to 5 days.

Stems:

*Basal stems arising from rhizomes*.—

*Length*.—Up to 50 cm by late summer.

*Diameter*.—3 mm to 4 mm.

*Color*.—Newly emerging growth and new shoot growth 140A. Mature stems 141B.

*Shape*.—Cylindrical.

*Texture*.—Pubescent, hairs fine, off-white 155C, 0.5 mm in length.

*Strength*.—Stiff, wiry. Stems will arch at 45 cm to 50 cm in length.

*Lateral stems*.—Rarely present. Where present, lateral stems arise very low down, at or slightly above soil surface.

Leaves:

*Type, arrangement*.—Simple, alternate.

*Attachment*.—Sessile.

*Quantity per stem*.—12 to 15.

*Shape*.—Elliptic.

*Length*.—8 cm to 10 cm.

*Width*.—2.5 cm to 3.5 cm.

*Venation*.—Parallel. Veins appear as furrows on adaxial surface and as ridges on abaxial surface.

*Texture*.—Smooth, glabrous, matte except adaxial surface of young foliage bright, glossy.

*Color* (*newly emerging foliage and young foliage in spring and early summer*).—

*Both surfaces*.—Bicolored, mid-dark green center ranging between 135B and 135C with broad yellow-gold edges ranging through and between 9A to 9C. Yellow-gold margins extend approximately 9 mm inward from the leaf margin and represent approximately 50% off leaf surface area.

*Color* (*foliage from mid-summer through fall*).—

*Both surfaces*.—Bicolored, blue-green 122B with occasional interveinal grey-green stripes 189B and 189C. Cream then white colored edges ranging between 155A and NN155D. White or cream edges represent approximately 20% of leaf surface area.

*Margin*.—Entire.

*Apex*.—Acute.

*Base*.—Clasping.

Inflorescence:

*Type*.—Cyme consisting of star-shaped flowers borne singly or in groups of two to five flowers.

*Dimensions*.—5 cm to 8 cm in diameter, 5 cm to 12 cm. in overall height, according to number of flowers in each inflorescence.

*Bloom period*.—Mid-late summer until fall.

Pedicel:

*Length*.—2.5 cm to 3.5 cm.

*Diameter*.—3 mm.

*Shape*.—Round.

*Color*.—141C.

*Texture*.—Pubescent, hairs fine, off-white 155C, 0.5 mm in length.

Buds:

*Length*.—1.5 cm.

*Diameter*.—0.75 cm.

*Shape*.—Truncated cone, apex rounded, base truncate.

*Color*.—59A except base N144A

*Surface*.—Pubescent, hairs fine, off-white 155C, 0.5 mm in length.

*Nectaries*.—Appear as fused spherical pouches attached to base of each of the three wider developing tepals, approximately 1.5 mm in diameter, color 141C.

Flowers:

*Type*.—Actinomorphic, upward facing.

*Perianth*.—Six petal-like tepals, unfused, of which three narrow and three wide.

*Dimensions*.—5 cm in diameter, up to 1 cm. in height.

*Longevity*.—3 to 5 days.

*Persistence*.—None.

*Fragrance*.—None.

Tepals: Six in number, 3 narrow, 3 wide.

*Narrow tepals*.—Shape: Rectangular, slight tapering towards base. Apex, base: both truncate. Dimensions: 20 mm to 25 mm in length, 4 mm to 5 mm in width. Color (both surfaces): Pale pink 65D except base 22D. Tepal spots N78A. Tepal spots: Approximately 20 to 25 per narrow tepal, mostly round, occasionally slightly oval, 0.5 mm in diameter, color N74A. Texture: Smooth, glabrous.

*Wide tepals*.—Shape: Broadly obovate, narrowing towards base. Apex: Rounded with single notch approximately 1 mm. in depth. Base: Truncate. Dimensions: 20 mm to 25 mm in length, 10 mm to 12 mm in width. Color (both surfaces): Red-purple N74B except paler tepal median ranging between white 155B and pale pink 65D. Tepal base 22D. Tepal spots N78A. Texture: Smooth, glabrous.

Reproductive organs:

*Stamens*.—6.

*Filaments*.—15 mm in length, color 161D.

*Anthers*.—Ovoid, 3 mm in length, 2 mm in diameter, color 165C.

*Pollen*.—Absent.

*Pistil*.—1, 18 mm in length.

*Style*.—3 in number, each 4 mm in length including terminal fork.

*Style color*.—35C with oval spots color 45B.

*Style glands*.—7 to 10 in number, 1 mm to 1.5 mm in length, color 161D, attached at right angles to style surface.

*Ovary*.—Not observed.

*Nectaries*.—Present as fused bi-valved pouch at base of each wide tepal; 5 mm to 6 mm in width, 5 mm in length, color 175C when flower fully developed.

Seed, fruit: None observed.

Disease and pest resistance or susceptibility: None observed.

COMPARISON WITH PARENTAL LINES AND KNOWN VARIETY

'KRISTEN' is distinguishable from the parent *Tricyrtis formosana* 'Samurai' as follows. Whereas the leaves of 'KRISTEN' are variegated green with bright wide and golden yellow edges from spring into summer, the leaves of 'Samurai' are paler green with a narrower light yellow or chartreuse edge. In addition, plants of 'Samurai' are taller at 60 cm in height whereas 'KRISTEN' achieves a height of 45 cm to 50 cm.

'KRISTEN' may be compared with the variegated variety *Tricyrtis formosana* 'Gilt Edge' (not patented) whose leaves are pale green with a thin white edge. In addition, plants of 'KRISTEN' exhibit greater vigor than plants of 'Gilt Edge'.

I claim:

1. A new and distinct variety of *Tricyrtis* plant named 'KRISTEN' as described and illustrated.

* * * * *